United States Patent
Shao et al.

(10) Patent No.: US 8,258,431 B2
(45) Date of Patent: Sep. 4, 2012

(54) CARDIAC LEAD COIL STRIPPING

(75) Inventors: Haiping Shao, Plymouth, MN (US);
Kenneth L. Gunter, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 259 days.

(21) Appl. No.: 12/846,595

(22) Filed: Jul. 29, 2010

(65) Prior Publication Data

US 2011/0062129 A1     Mar. 17, 2011

Related U.S. Application Data

(60) Provisional application No. 61/243,407, filed on Sep. 17, 2009.

(51) Int. Cl.
*B23K 26/00*     (2006.01)

(52) U.S. Cl. .................................................. 219/121.85

(58) Field of Classification Search ............. 219/121.85, 219/121.6, 146.22, 137 R; 607/115–128, 607/36; 29/867
See application file for complete search history.

(56) References Cited

U.S. PATENT DOCUMENTS

| | | | |
|---|---|---|---|
| 5,925,069 A | 7/1999 | Graves et al. | |
| 6,141,593 A | 10/2000 | Patag | |
| 6,374,488 B1 | 4/2002 | McLean et al. | |
| 6,401,334 B1 | 6/2002 | McLean et al. | |
| 2006/0235499 A1* | 10/2006 | Heil et al. | 607/127 |
| 2007/0173915 A1 | 7/2007 | Westlund | |
| 2007/0250143 A1* | 10/2007 | Sommer | 607/116 |

* cited by examiner

*Primary Examiner* — Dao H Nguyen
*Assistant Examiner* — Tram H Nguyen
(74) *Attorney, Agent, or Firm* — Faegre Baker Daniels LLP

(57) ABSTRACT

An implantable lead may have a distal assembly including a coupler, a terminal pin and a conductive member rotatably secured to both the coupler and the terminal pin. The conductive member may include a coating that is at least partially removed before securing the conductive member to the coupler and the terminal pin. The coating may be removed in a process combining, in sequence, an IR laser and a UV laser.

20 Claims, 10 Drawing Sheets

CARDIAC LEAD COIL STRIPPING

CROSS-REFERENCE TO RELATED APPLICATIONS

This application claims the benefit under 35 U.S.C. §119 (e) to U.S. Provisional Patent Application No. 61/243,407, filed on Sep. 17, 2009, entitled "CARDIAC LEAD COIL STRIPPING," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is a method of preparing a conductive member for use in a cardiac lead. The conductive member includes a coil having a coating. The coil is stretched to expose at least a portion of the coating. At least a portion of the stretched region of the coil is subjected to stripping energy to remove a substantial portion of the coating while forming a clean edge between a stripped region and a non-stripped region, leaving a residual coating within the stripped region. The stripped region is subjected to cleaning energy to remove the residual coating without damaging the coil.

In Example 2, the method of Example 1 in which the coating includes a copolymer of ethylene and tetrafluoroethylene (ETFE).

In Example 3, the method of Example 1 or Example 2 in which subjecting at least a portion of the stretched region of the coil to stripping energy includes subjecting at least a portion of the stretched region of the coil to energy from an IR laser.

In Example 4, the method of Example 3 in which the coil is subjected to IR laser energy at a wavelength of about 9.4 micrometers, a pulse repetition rate of about 12 Hz and for a duration about 12 seconds.

In Example 5, the method of Example 4 or Example 5, further including rotating the coil at a rotational speed of about 720 degrees per second while subjecting the coil to IR laser energy.

In Example 6, the method of any of Examples 1-5 in which subjecting the stripped region to cleaning energy includes subjecting the stripped region to energy from a UV laser.

In Example 7, the method of Example 6 in which the coil is subjected to UV laser energy of about 193 nanometers, a pulse repetition rate of about 25 Hz and for a duration about 4 seconds.

In Example 8, the method of Example 6 or Example 7, further including rotating the coil at a rotational speed of about 90 degrees per second while subjecting the coil to UV laser energy.

In Example 9, the method of any of Examples 1-8 in which forming a clean edge between a stripped region and a non-stripped region includes removing a substantial amount of the coating in the stripped region near to the non-stripped region while not damaging the coating in the non-stripped region near to the stripped region.

In Example 10, the method of any of Examples 1-9 in which the stripped region, subsequent to the cleaning step, is coating-free.

In Example 11, the method of Example 10 in which the stripped region, subsequent to the cleaning step, is free of orange peel that would indicate melting damage to the coil.

Example 12 is a method for preparing a conductive member for use in a cardiac lead. The conductive member includes a coiled metal filar having an ETFE coating. The coil is stretched to expose at least a portion of the ETFE coating. At least a portion of the stretched region of the coil is exposed to energy from an IR laser to remove a substantial portion of the ETFE coating while forming a clean edge between a stripped region and a non-stripped region and leaving a residual ETFE coating within the stripped region. The stripped region is subjected to energy from a UV laser to remove the residual ETFE coating from the stripped region without damaging the coil such that the stripped region is at least substantially free of fluorine.

In Example 13, the method of Example 12 in which the coil is subjected to IR laser energy at a wavelength of about 9.4 micrometers, a pulse repetition rate of about 12 Hz and for a duration about 12 seconds.

In Example 14, the method of Example 12 or Example 13, further including rotating the coil at a rotational speed of about 720 degrees per second while subjecting the coil to IR laser energy.

In Example 15, the method of any of Examples 12-14 in which the coil is subjected to UV laser energy at a wavelength of about 193 nanometers, a pulse repetition rate of about 25 Hz and for a duration about 4 seconds.

In Example 16, the method of any of Examples 12-15, further including rotating the coil at a rotational speed of about 90 degrees per second while subjecting the coil to UV laser energy.

In Example 17, the method of any of Examples 12-16 in which forming a clean edge between a stripped region and a non-stripped region includes removing a substantial amount of the ETFE coating in the stripped region near to the non-stripped region while not damaging the ETFE coating in the non-stripped region near to the stripped region.

Example 18 is a method of preparing a conductive member for use in a cardiac lead. The conductive member includes a coil and an ETFE coating disposed on the coil. A substantial portion of the ETFE coating is removed via a photothermal process. A remaining portion of the ETFE coating is removed via a photochemical process.

In Example 19, the method of Example 18 in which removing a substantial portion of the ETFE coating via a photothermal process includes subjecting the ETFE coating to laser energy having a wavelength of about 9 micrometers.

In Example 20, the method of Example 18 or Example 19 in which removing a remaining portion of the ETFE coating via a photochemical process includes subjecting the ETFE coating to laser energy having a wavelength of about 193 nanometers.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
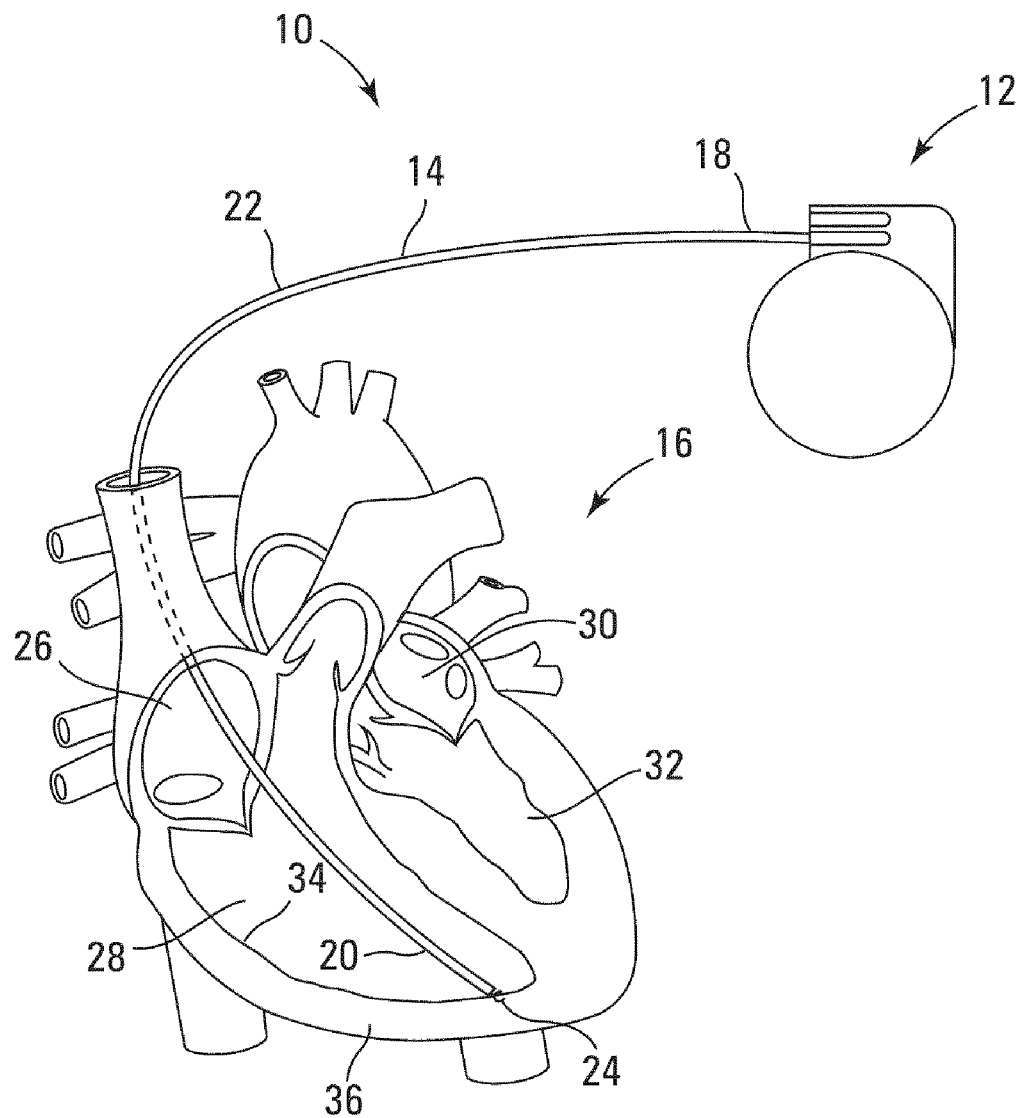
FIG. 1 is a combined cutaway and perspective view of an implantable medical device and lead in accordance with an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes a fixation helix 24, which as will be discussed in greater detail below, locates and/or secures the distal region 20 within the heart 16. In the illustrated embodiment, the cardiac lead 14 is an active fixation lead. In some embodiments, the cardiac lead 14 may be a passive fixation lead, and thus may not include the fixation helix 24.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. Rather, in some embodiments, other components of the lead 14 are electrically active.

Figure 2:
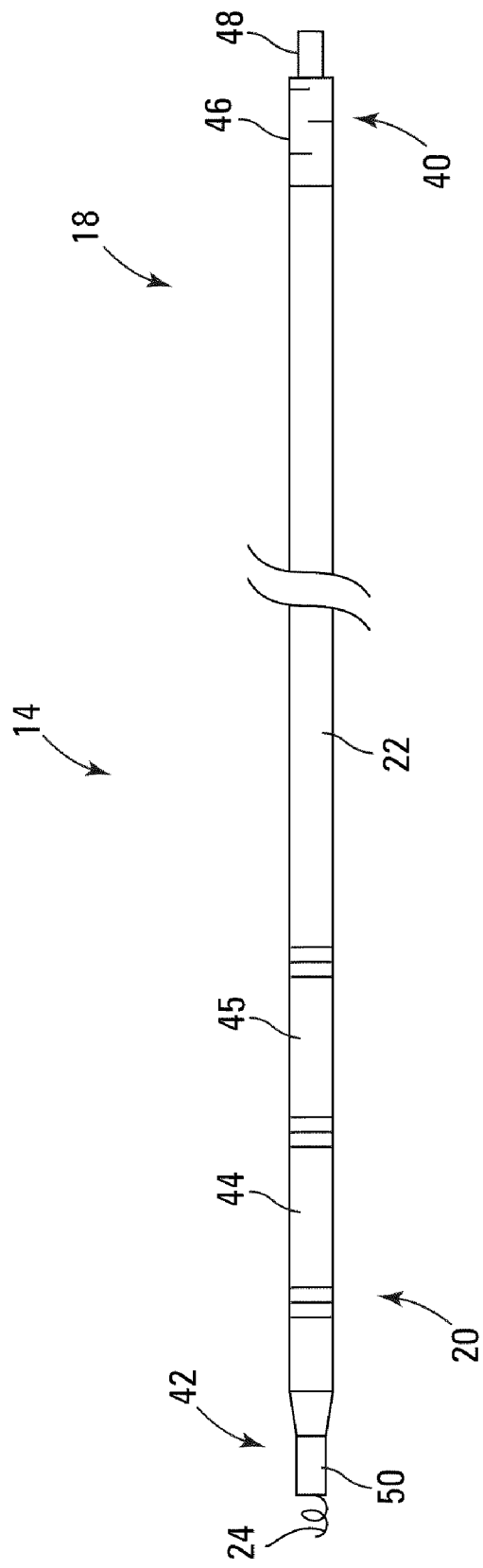
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on the pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture extending therethrough in order to accommodate a guide wire or an insertion stylet.

The distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include a structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, nickel, tungsten, tantalum, iridium, platinum, titanium, palladium, stainless steel as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

Figure 3:
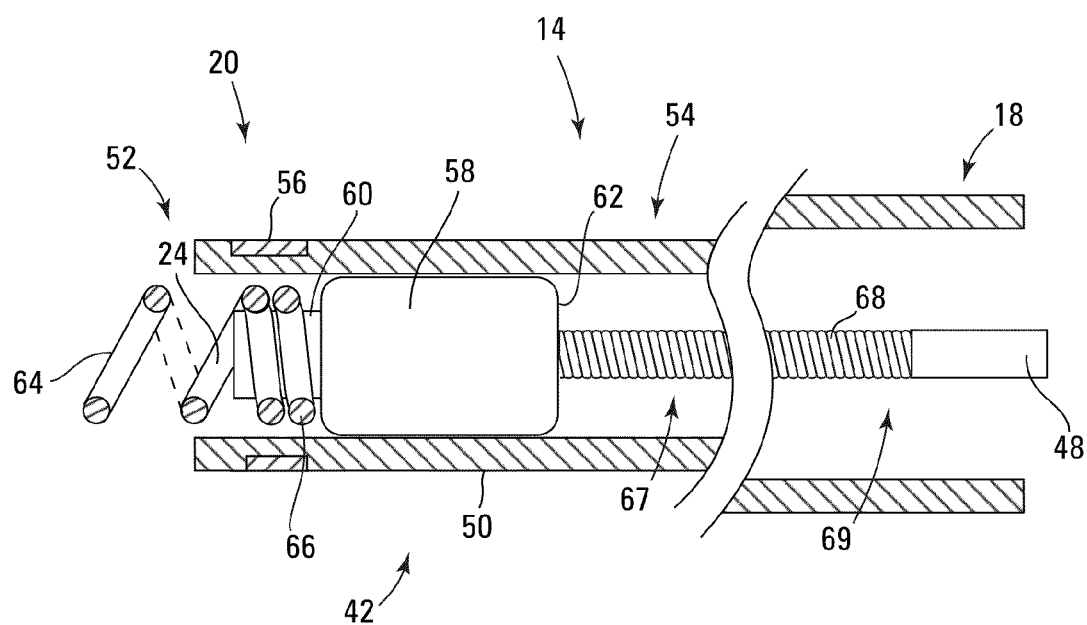
FIG. 3 is a cross-sectional view of the lead of FIG. 1.

FIG. 3 is a cross-sectional view of the lead 14. As shown in FIG. 3, the housing 50 includes a distal region 52 and a proximal region 54. The housing 50 is, in general, relatively rigid or semi-rigid. In some embodiments, the housing 50 is made of an electrically conductive material such as Elgiloy, MP35N, nickel, tungsten, tantalum, iridium, platinum, titanium, palladium, stainless steel as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments the distal assembly 42 may include a radiopaque element disposed under the drug eluting collar 56.

The distal assembly 42 includes a coupler 58 that has a distal portion 60 and a proximal portion 62. In some embodiments, the coupler 58 is formed of a metallic material and is configured to move longitudinally and/or rotationally with respect to the housing 50. In some embodiments, as illustrated, the distal portion 60 may have a relatively smaller diameter (relative to the proximal portion 62) in order to accommodate the fixation helix 24. While not illustrated, in some embodiments the proximal portion 62 is configured to accommodate a seal that provides a seal between the coupler 58 and the housing 50.

The fixation helix 24 has a distal region 64 and a proximal region 66. The proximal region 66 of the fixation helix 24 is secured to the distal portion 60 of the coupler 58. One or more attachment methods are used to secure the fixation helix 24 to the coupler 58. In some embodiments, the proximal region 66 of the fixation helix 24 is welded or soldered onto the distal portion 60 of the coupler 58. In some embodiments, the proximal region 66 of the fixation helix 24 has an inner diameter that is less than an outer diameter of the distal portion 60 of the coupler 58, and thus is held in place via compressive forces. In some embodiments the fixation helix 24 is adhesively secured to the distal portion 60 of the coupler 58. In some embodiments, multiple attachment methods are used.

A conductor member 68 has a distal region 67 and a proximal region 69. The distal region 67 of the conductor member 68 is secured to the proximal portion 62 of the coupler 58, and extends proximally through the lead body 22 to the connector assembly 40. The proximal region 69 of the conductor member 68 is coupled to the terminal pin 48 such that rotation of the terminal pin 48 causes the conductor member 68 to rotate.

In some embodiments, the conductor member 68 includes or is otherwise formed from a metallic coil. The coupler 58 provides an electrical connection between the conductor member 68 and the fixation helix 24. In some embodiments, the distal region 67 of the conductor member 68 is welded to the proximal portion 62 of the coupler 58. In some embodiments, the proximal region 69 of the conductor member 68 is welded to the terminal pin 48.

In some embodiments, the conductor member 68 includes a coating that is disposed on the conductor member 68. In some embodiments, the conductor member 68 is formed from one or more coated filars that are wound or coiled to form the conductor member 68. The coating can have a thickness in the range of about 10 micrometers to several tens of micrometers and can be selected to provide desired properties to the conductor member 68. In some embodiments, the coating is an electrically insulative material such as ETFE, which is a co-polymer of ethylene and tetrafluoroethylene.

As noted above, portions of the conductor member 68 may be welded to lead components such as the coupler 58 or the terminal pin 48. In some cases, it may be useful to remove at least a portion of the coating to facilitate welding or mechanical fixation methods such as crimping or swaging as the coating can, in some instances, interfere with subsequent processing steps. In some embodiments, at least a portion of the coating can be removed in a laser stripping process as schematically shown in FIG. 4.

Figure 4:
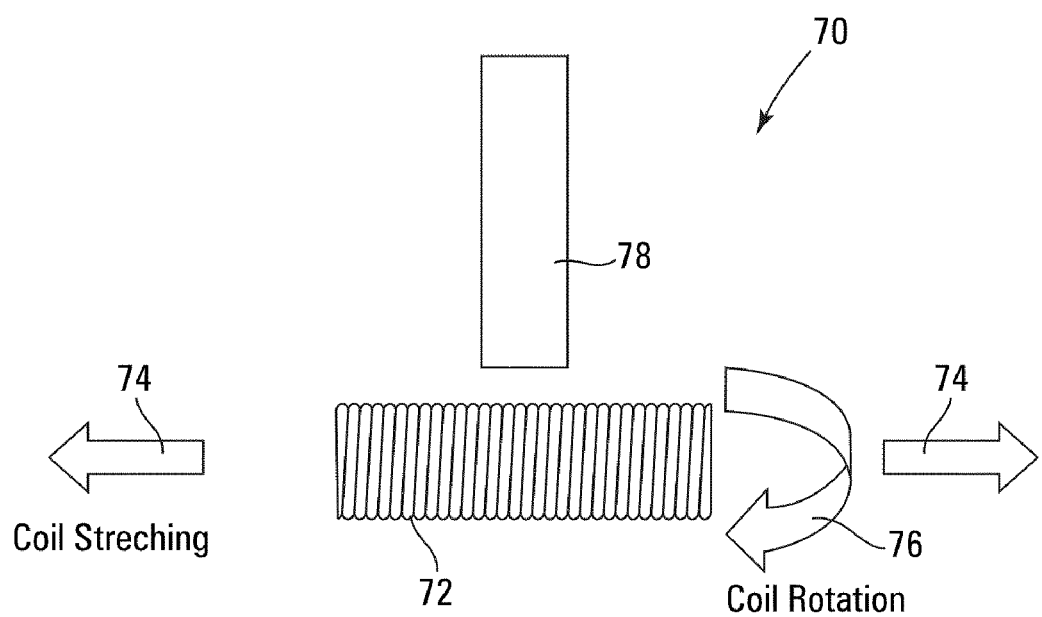
FIG. 4 is a schematic illustration of a stripping apparatus useful in making the lead of FIG. 1.

FIG. 4 is a schematic illustration of a coil stripping apparatus 70. The coil stripping apparatus 70 is configured to stretch a coil 72 as indicated by arrows 74. In some embodiments, either end of the coil 72 may be clamped or otherwise secured by structure that can apply a stretching force. The relative amount that the coil 72 is stretched is at least partially a function of the initial filar spacing. For example, if the coil 72 is formed such that the initial filar spacing is quite small, the coil 72 may be stretched further than if the initial filar spacing was larger.

In some embodiments, as illustrated, the coil 72 is also rotated, as shown by arrow 76. The apparatus 70 includes a laser 78. In some embodiments, not illustrated, the coil 72 may remain stationary while the laser 78 rotates and/or translates around the coil 72. In some embodiments, one or more beam splitters can be used to subject parts of the coil 72 to energy from the laser 78. In some embodiments, the use of one or more beam splitters may permit holding the coil 72 and/or the laser 78 stationary.

In some embodiments, the coil 72 can be manually stretched to be clamped or otherwise secured to the structure at either end. In some embodiments, the coil 72 can be clamped or otherwise secured to the aforementioned structure, which can then automatically stretch the coil 72 to a desired length or to a desired elongation. In some embodiments, the coil 72 can be clamped or otherwise secured to the structure at either end that are aligned along an axis and are configured to be rotated about the axis. In some embodiments, the coil 72 may represent a single conductive member 68. In some cases, the coil 72 may represent a plurality of conductive members 68 that can be cut out of the coil 72 once the coating has been removed in appropriate locations along the coil 72.

A variety of lasers can be used as the laser 78. In some instances, the laser 78 is an IR laser such as a short pulse $CO_2$ laser, which has a pulse width in the range of a few microseconds or less. In some cases, the laser 78 is a short pulse UV laser such as an Excimer laser, which has a pulse width of about 25 microseconds. In some embodiments, the laser 78 represents both an IR laser and a UV laser that are used sequentially in stripping the coating off of at least a portion of the coil 72.

While using an IR laser to remove a coating such as an ETFE coating can leave a residual coating on the coil, using a UV laser can completely remove the coating in a single step. However, in some cases, use of a UV laser to remove the coating can damage the coil and leave an orange-peel morphology caused by excessive heating. In accordance with the present invention, it has been determined these two techniques can be combined in a cost-effective way that safely and completely removes the coating without damaging the coil. In some embodiments, combining these two techniques can actually help to smooth the metal surface, thereby improving the fatigue resistance of the coil.

In some embodiments, a short pulse IR laser can be used to remove a substantial portion of the coating on the coil 72. The short pulse IR laser removes the ETFE coating in a photothermal process in which photons react with and heat the ETFE. The short pulse IR laser provides for a clean edge. Forming a clean edge can be defined as removing a substantial amount of the coating in a stripped region near to a non-stripped region while not damaging the coating in the non-stripped region near to the stripped region. In other words, the remaining coating is not excessively melted or otherwise damaged.

In some embodiments, a substantial amount of an EFTE coating can be removed by subjecting the coil 72 to IR laser energy at a wavelength of about 9.4 micrometers, a pulse repetition rate of about 12 Hz and for a duration about 12 seconds. In some instances, the coil 72 is rotated at a rotational speed of about 720 degrees per second (about 2 revolutions per second) while operating the IR laser. These process parameters have been found to remove most of the ETFE coating, leaving only a residual coating having a thickness of a few micrometers.

In some embodiments, at least substantially all of the remaining or residual ETFE coating can be removed by subjecting the coil 72 to energy from a UV laser. In some embodiments, the UV laser removes enough of the remaining or residual ETFE coating to enable subsequent welding or other processing steps. In some embodiments, all or substantially all of the remaining or residual ETFE coating is removed by the UV laser, leaving the coil 72 at least substantially free of fluorine, meaning that if any fluorine (indicating the presence of ETFE) remains, it is present at an amount low enough to permit welding or other processing steps.

The UV laser removes the ETFE coating in a photochemical process in which impinging photons disrupt molecules within the ETFE coating. In some embodiments, the remaining or residual ETFE coating can be removed by subjecting the coil 72 to UV laser energy at a wavelength of about 193 nanometers, a pulse repetition rate of about 25 Hz and for a duration of about 4 seconds. In some instances, the coil 72 is rotated at a rotational speed of about 90 degrees per second (about a quarter revolution per second) while operating the UV laser.

Figure 5:
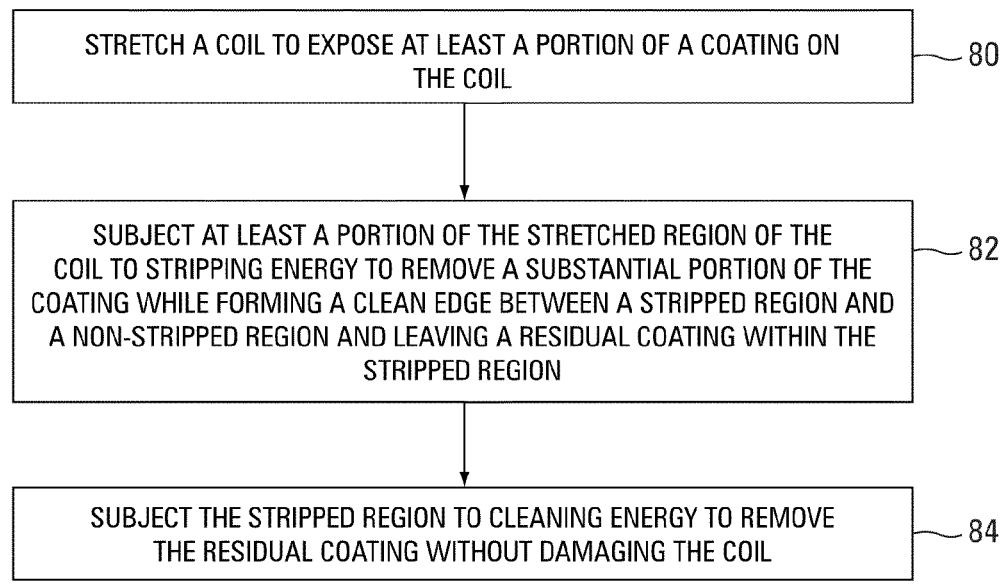
FIG. 5 is a flow diagram illustrating a process useful in making the lead of FIG. 1.

FIG. 5 is a flow diagram showing a method that may be used in stripping a coil such as the conductive member 68. A coil such as the coil 72 is stretched to expose at least a portion of a coating on the coil, as generally referenced at block 80. At block 82, at least a portion of the stretched region of the coil is subjected to stripping energy to remove a substantial portion of the coating while forming a clean edge between a stripped region and a non-stripped region and while leaving a residual coating within the stripped region. In some embodiments, the stripping energy can be supplied by an IR laser. At block 84, the stripped region is then subjected to cleaning energy to remove the residual coating without damaging the coil. In some embodiments, the cleaning energy can be supplied by a UV laser.

Figure 6:
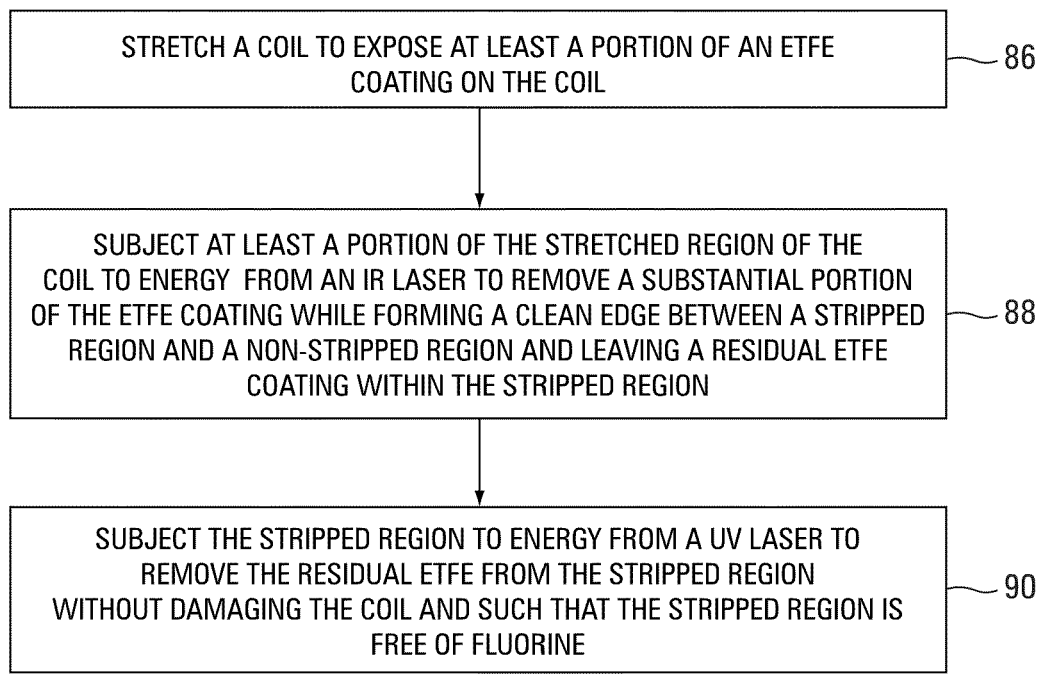
FIG. 6 is a flow diagram illustrating a process useful in making the lead of FIG. 1.

FIG. 6 is a flow diagram showing a method that may be used in stripping a coil such as the conductive member 68. A coil such as the coil 72 is stretched to expose at least a portion of an ETFE coating on the coil, as generally seen at block 86. At block 88, at least a portion of the stretched region of the coil is subjected to energy from an IR laser to remove a substantial portion of the ETFE coating while forming a clean edge between a stripped region and a non-stripped region and while leaving a residual coating within the stripped region. At block 90, the stripped region is then subjected to energy from a UV laser to remove the residual ETFE coating without damaging the coil.

Figure 7:
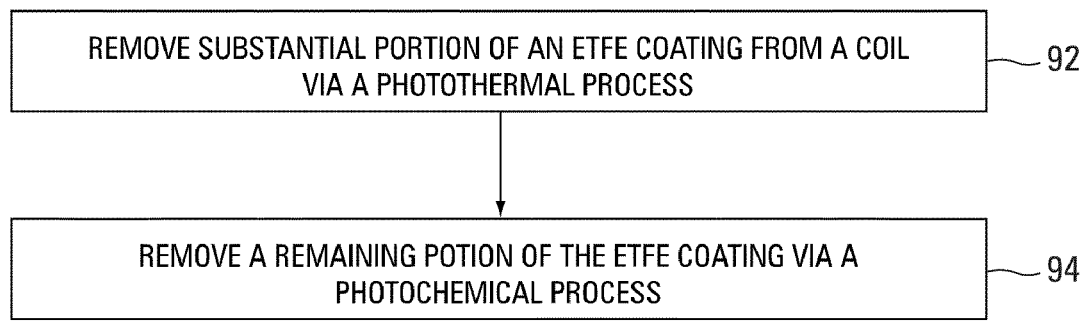
FIG. 7 is a flow diagram illustrating a process useful in making the lead of FIG. 1.

FIG. 7 is a flow diagram showing a method that may be used in stripping a coil such as the conductive member 68. At block 92, a substantial portion of an ETFE coating is removed from a coil using a photothermal process. In some embodiments, the photothermal process may include subjecting the coating to IR laser energy having a wavelength of about 9 micrometers. The remaining portion of the ETFE coating is removed via a photochemical process, as generally referenced at block 94. In some embodiments, the photochemical process may include subjecting the residual coating to UV laser energy having a wavelength of about 193 nanometers.

EXAMPLE

To demonstrate the usefulness of the invention, a coil formed from an ETFE coated filar was stripped using, in sequence, an IR laser to remove a substantial portion of the ETFE coating and a UV laser to remove the remaining portion of the ETFE coating. An apparatus such as that shown in FIG. 4 was used to stretch and rotate the coil. The coil tested was formed from a filar made of MP35N having a silver core and having a filar diameter of 0.004 inches. The ETFE coating on the filar had a thickness of 0.001 inches and the coil had an overall diameter of 0.060 inches. The coil was stretched about 20 percent.

In a stripping step, a $CO_2$ laser having a wavelength of 9 micrometers was used. The $CO_2$ laser had a fluence of 6.2 $J/cm^2$. A pulse repetition rate of 12 Hz was used. The coil was rotated a total of 24 rotations at a rotation speed of 720 degrees per second. The coil was subjected to a total of 147 pulses over a period of 12 seconds.

In a subsequent cleaning step, a UV laser having a wavelength of 193 nanometers was used. The UV laser had a fluence of 0.7 $J/cm^2$. A pulse repetition rate of 25 Hz was used. The coil was rotated once at a rotation speed of 90 degrees per second. The coil was subjected to a total of 100 pulses over a period of 4 seconds.

Figure 8:
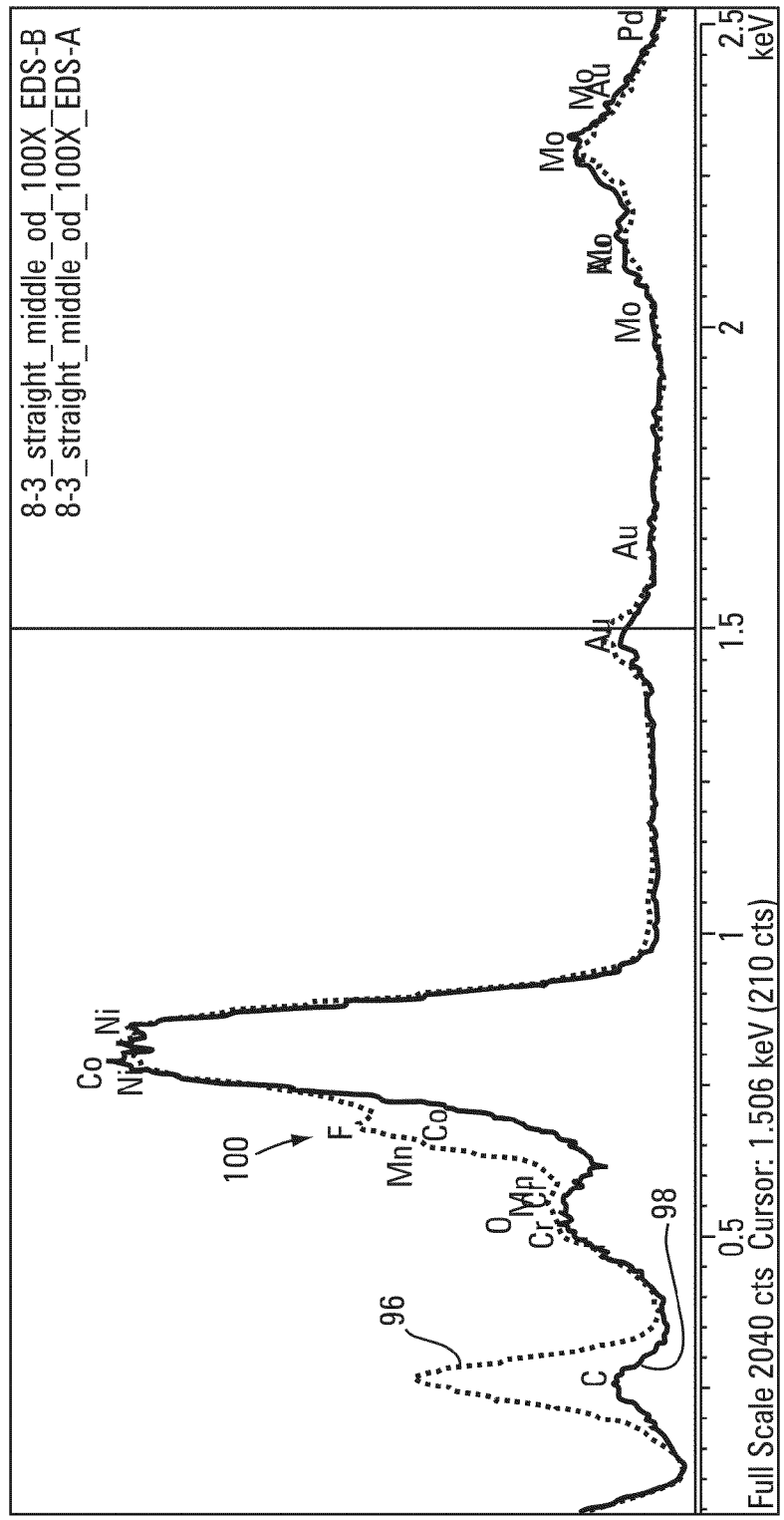
FIG. 8 is an Energy Dispersed Spectrographic (EDS) graph providing experimental results.

FIG. 8 is an electron-dispersive X-ray spectroscopy (EDS) spectrum showing results of the stripping and cleaning steps. FIG. 8 includes a first line 96 that represents the results of the stripping step and a second line 98 that represents the results of the subsequent cleaning step. As indicated by an arrow 100, the first line 96 includes a peak indicating the presence of fluorine. This means that the ETFE coating has not been completely removed. The second line 98, however, does not have this fluorine peak, meaning that the cleaning step has removed all of the ETFE coating.

Figure 9:
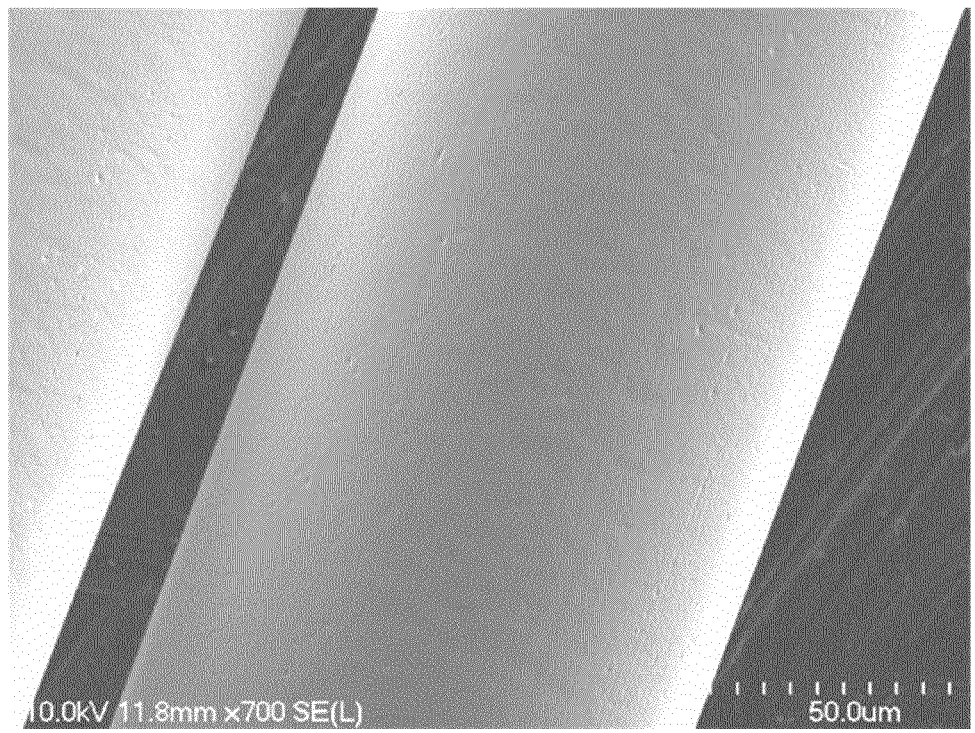
FIG. 9 is a Scanning Electron Microscope (SEM) image providing experimental results.
Figure 10:
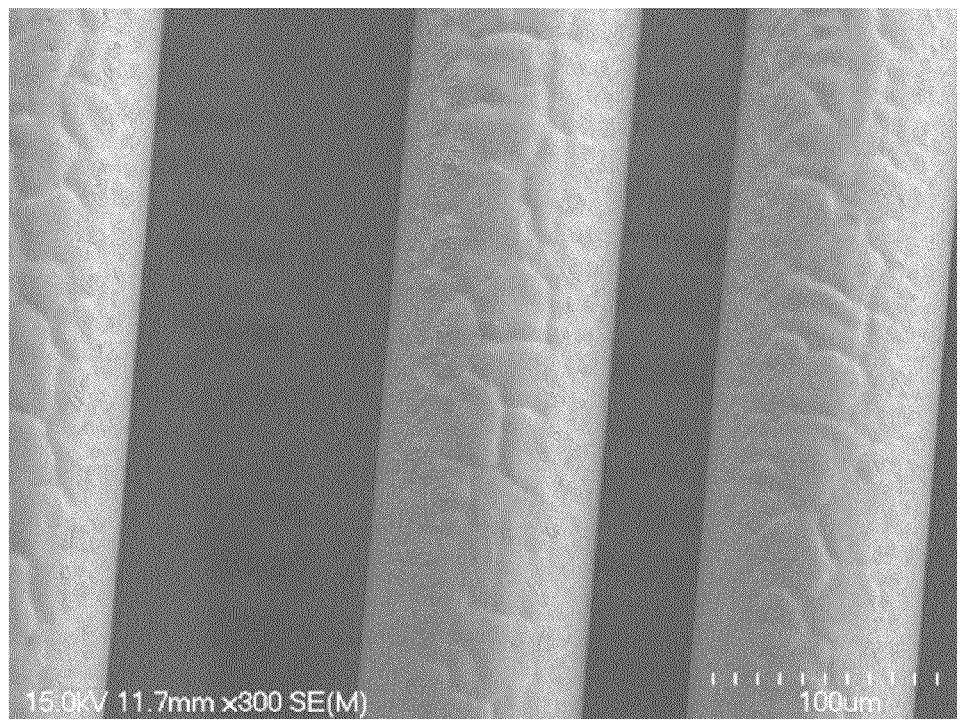
FIG. 10 is a comparative SEM image.

FIG. 9 is an electronic image of a SEM (scanning electron microscopy) image showing the stripped coil. As can be seen, the individual filars are clean and undamaged, with no presence of an orange peel morphology that would otherwise indicate damage to the metal filar. For comparison purposes, FIG. 10 is an electronic image of a SEM image illustrating an orange peel morphology.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of preparing a conductive member for use in a cardiac lead, the conductive member including a coil having a coating, the method comprising:
   stretching the coil to expose at least a portion of the coating;
   subjecting at least a portion of the stretched region of the coil to stripping energy to remove a substantial portion of the coating while forming a clean edge between a stripped region and a non-stripped region and leaving a residual coating within the stripped region; and
   subjecting the stripped region to cleaning energy to remove the residual coating without damaging the coil.

2. The method of claim 1, wherein the coating comprises a copolymer of ethylene and tetrafluoroethylene.

3. The method of claim 1, wherein subjecting at least a portion of the stretched region of the coil to stripping energy comprises subjecting at least a portion of the stretched region of the coil to energy from an IR laser.

4. The method of claim 3, wherein the coil is subjected to IR laser energy at a wavelength of about 9.4 micrometers, a pulse repetition rate of about 12 Hz and for a duration about 12 seconds.

5. The method of claim 4, further comprising rotating the coil at a rotational speed of about 720 degrees per second while subjecting the coil to IR laser energy.

6. The method of claim 1, wherein subjecting the stripped region to cleaning energy comprises subjecting the stripped region to energy from a UV laser.

7. The method of claim 6, wherein the coil is subjected to UV laser energy at a wavelength of about 193 nanometers, a pulse repetition rate of about 25 Hz and for a duration about 4 seconds.

8. The method of claim 7, further comprising rotating the coil at a rotational speed of about 90 degrees per second while subjecting the coil to UV laser energy.

9. The method of claim 1, wherein forming a clean edge between a stripped region and a non-stripped region comprises removing a substantial amount of the coating in the stripped region near to the non-stripped region while not damaging the coating in the non-stripped region near to the stripped region.

10. The method of claim 1, wherein the stripped region, subsequent to the cleaning step, is coating-free.

11. The method of claim 10, wherein the stripped region, subsequent to the cleaning step, is free of orange peel that would indicate melting damage to the coil.

12. A method of preparing a conductive member for use in a cardiac lead, the conductive member including a coiled metal filar having an ETFE coating, the method comprising:
   stretching the coil to expose at least a portion of the ETFE coating;
   subjecting at least a portion of the stretched region of the coil to energy from an IR laser to remove a substantial portion of the ETFE coating while forming a clean edge between a stripped region and a non-stripped region and leaving a residual ETFE coating within the stripped region; and
   subjecting the stripped region to energy from a UV laser to remove the residual ETFE coating from the stripped region without damaging the coil such that the stripped region is at least substantially free of fluorine.

13. The method of claim 12, wherein the coil is subjected to IR laser energy at a wavelength of about 9.4 micrometers, a pulse repetition rate of about 12 Hz and for a duration about 12 seconds.

14. The method of claim 13, further comprising rotating the coil at a rotational speed of about 720 degrees per second while subjecting the coil to IR laser energy.

15. The method of claim 12, wherein the coil is subjected to UV laser energy at a wavelength of about 193 nanometers, a pulse repetition rate of about 25 Hz and for a duration about 4 seconds.

16. The method of claim 15, further comprising rotating the coil at a rotational speed of about 90 degrees per second while subjecting the coil to UV laser energy.

17. The method of claim 12, wherein forming a clean edge between a stripped region and a non-stripped region comprises removing a substantial amount of the ETFE coating in the stripped region near to the non-stripped region while not damaging the ETFE coating in the non-stripped region near to the stripped region.

18. A method of preparing a conductive member for use in a cardiac lead, the conductive member including a coil and an ETFE coating disposed on the coil, the method comprising:
   removing a substantial portion of the ETFE coating via a photothermal process; and
   removing a remaining portion of the ETFE coating via a photochemical process.

19. The method of claim 18, wherein removing a substantial portion of the ETFE coating via a photothermal process comprises subjecting the ETFE coating to laser energy having a wavelength of about 9 micrometers.

20. The method of claim 18, wherein removing a remaining portion of the ETFE coating via a photochemical process comprises subjecting the ETFE coating to laser energy having a wavelength of about 193 nanometers.

* * * * *